(12) United States Patent
Smotkin

(10) Patent No.: US 6,692,856 B2
(45) Date of Patent: Feb. 17, 2004

(54) HIGH THROUGHPUT SCREENING DEVICE FOR COMBINATORIAL CHEMISTRY

(75) Inventor: Eugene S. Smotkin, Chicago, IL (US)

(73) Assignee: NuVant Systems, LLC, San Juan, PR (US)

(*) Notice: Subject to any disclaimer, the term of this patent is extended or adjusted under 35 U.S.C. 154(b) by 0 days.

(21) Appl. No.: 09/907,628

(22) Filed: Jul. 19, 2001

(65) Prior Publication Data

US 2002/0009627 A1 Jan. 24, 2002

Related U.S. Application Data

(60) Provisional application No. 60/219,107, filed on Jul. 19, 2000.

(51) Int. Cl.[7] ............... H01M 8/10; H01M 4/86; G01N 27/00
(52) U.S. Cl. ............... 429/30; 429/32; 429/40; 429/44; 204/410; 204/411; 204/421
(58) Field of Search ............... 429/30, 32, 40, 429/44; 204/403.02, 403.03, 409, 410, 411, 421, 422, 424, 426, 432

(56) References Cited

U.S. PATENT DOCUMENTS

| | | | |
|---|---|---|---|
| 4,820,386 A | | 4/1989 | LaConti et al. |
| 5,830,343 A | | 11/1998 | Hintsche et al. |
| 5,869,202 A | * | 2/1999 | Marchetti ............... 429/30 |
| 5,879,828 A | | 3/1999 | Debe et al. |
| 5,985,113 A | | 11/1999 | Crome et al. |
| 6,030,718 A | | 2/2000 | Fuglevand et al. |
| 6,136,412 A | | 10/2000 | Spiewak et al. |
| 6,187,164 B1 | | 2/2001 | Warren et al. |
| 6,528,191 B1 | * | 3/2003 | Senner ............... 429/12 |
| 2002/0122972 A1 | * | 9/2002 | Klitsner et al. ............... 429/42 |

FOREIGN PATENT DOCUMENTS

| | | | |
|---|---|---|---|
| WO | WO00/04362 | | 1/2000 |
| WO | WO 00/69007 | * | 11/2000 |

OTHER PUBLICATIONS

Thomas Bein "Efficient Assays for Combinatorial Methods for the Discovery of Catalysts" Angew. Chem. Int. Ed. 1999, 38, No. 3. (No Month).

* cited by examiner

Primary Examiner—Randy Gulakowski
Assistant Examiner—Jonathan Crepeau
(74) Attorney, Agent, or Firm—Morrison & Foerster LLP

(57) ABSTRACT

A high throughput screening device for combinatorial chemistry, comprising a membrane electrode assembly, an array of sensor electrodes and one or more common electrodes, wherein a total cross-sectional area of the one or more common electrodes is greater than a sum of the cross-sectional areas of the sensor electrodes is disclosed. This device obtains performance data from each and every array electrode simultaneously and does not require the movement of any electrode during data acquisition. Some application among many possible applications of the device of this invention is in the development and evaluation of catalysts (anode and cathode catalysts) for fuel cells and electrolysis systems.

20 Claims, 9 Drawing Sheets

HIGH THROUGHPUT SCREENING DEVICE FOR COMBINATORIAL CHEMISTRY

RELATED APPLICATIONS

This application claims priority from Provisional Application No. 60/219,107, filed Jul. 19, 2000, entitled "DEVICE FOR HIGH THROUGHPUT COMBINATORIAL SCREENING OF BULK ELECTROCATALYSTS" and to PCT application No. PCT/US01/22137, filed Jul. 16, 2001 having the same title as the present application, the entire disclosures of which are hereby incorporated herein by reference. This application is related to PCT application No. PCT/US01/20032, filed Jun. 22, 2001, and U.S. patent application No. 09/891,200, filed Jun. 25, 2001, which claims priority to U.S. provisional application No. 60/244,208, filed Oct. 31, 2000, both entitled, "HYDROGEN PERMEABLE MEMBRANE FOR USE IN FUEL CELLS AND PARTIAL CATALYSTS IN THE ANODE FUEL CELL COMPARTMENT," the entire disclosures of which are hereby incorporated herein by reference.

FIELD OF INVENTION

The present invention relates to a high throughput screening device for combinatorial chemistry, particularly, an array fuel cell (FC) that utilizes a one or more common electrode flow fields and an array electrode flow field that permits the evaluation of 25 fuel cell electro-catalyst surfaces simultaneously. The catalysts can be anode or cathode electro-catalyst candidates. Variations of catalysts compositions and/or methods of preparation can be evaluated in a high throughput mode.

BACKGROUND

Fuel cells are electrochemical devices that convert the chemical energy of a reaction directly into electrical energy. A fuel cell, although having components and characteristics similar to those of a typical battery, differs in several respects. The battery is an energy storage device. The maximum energy available is determined by the amount of chemical reactant stored within the battery itself. The battery will cease to produce electrical energy when the chemical reactants are consumed (i.e., discharged). In a secondary battery, recharging regenerates the reactants, which involves putting energy into the battery from an external source. The fuel cell, on the other hand, is an energy conversion device that theoretically has the capability of producing electrical energy for as long as the fuel and oxidant are supplied to the electrodes. In reality, degradation of catalyst performance, corrosion, and/or malfunction of components limit the practical operating life of fuel cells.

Fuel cells have been used on the space shuttle for a couple of decades. However, the fuel used in the fuel cells used on the space shuttle is pure, liquid hydrogen. Liquid hydrogen is expensive and requires cryogenics not practical for consumer use.

Gasoline, diesel and methane and alcohols are fuels that are practical for consumer use. However, gasoline, diesel, methane do not have adequate electrochemical reactivity to be used directly in state-of-the-art PEFCs for high power applications. A catalytic-chemical fuel processor (reformer) is required to convert these fuels to hydrogen-rich fuel gases. The reforming process yields $H_2$ diluted with $CO_2$, and low levels of CO. Within the operating temperature (T) range of polymer electrolyte fuel cells, the reformate prior to the water gas shift (WGS) and the preferential oxidation (PROX) reactor contains CO at the pph level, enough to shut down a Pt alloy catalyst. The WGS output contains about 1% CO, still enough to shut down the anode. A PROX unit is used to further reduce the CO content to the approximately 10-ppm tolerance limit of a typical anode catalyst (PtRu). The water-gas-shift reactor and the preferential oxidation unit are large units that reduce the overall power density of the fuel cell system. The development of CO tolerant anode catalysts would obviate the need for the PROX and WGS units and thus permit the design of more compact and efficient system. The development of superior anodes requires the discovery of new catalytic materials.

Another type of fuel cell is the direct methanol fuel cell (DMFC). The DMFC differs from reformate fuel cells because the fuel (methanol) is delivered directly to the anode catalytic surface, without prior reforming. A low temperatures (below 100° C.) methanol is the only liquid fuel that is sufficiently reactive for anode surfaces. An intermediate chemical that is formed during the oxidation of methanol is carbon monoxide (CO). CO poisons the DMFC anode catalytic surface in much the same way that CO poisons the surface of reformate anodes. Thus DMFCs require CO tolerant anodes as do reformate fuel cells. The development of superior DMFC anodes requires the development of better catalysts.

Progress in the area of catalyst discovery has been slow for a number of reasons. There are two electrodes in the fuel cell, the anode where the fuel is oxidized and the cathode where oxygen from air is reduced. A fuel cell, which only has one membrane electrode assembly (MEA), is termed a single cell. In catalysis work, only single cell assemblies are used for comparing catalysts.

If anode catalysts are being compared, it is important to ensure that the cathode electrode is not a variable (i.e. that the performance of the cathode from one test to another does not vary). It is important that the common electrode (the cathode in the case of searching for anode catalysts) is invariant so that changes in performance can be ascribed entirely to the anode performance. If the cathode performance varies from test to test, it becomes impossible to compare anode catalysts. Fuel cell systems are very complicated. In practice it is difficult to insure that the cathode is invariant.

Another issue is conditioning. After a catalyst layer has been inserted into the fuel cell, the layer must be conditioned prior to attempts to make steady state measurement. Conditioning is a process that usually involves operating the fuel cell for a period of time at a selected cell voltage or current. The effects of conditioning are not well understood. During the conditioning process, the catalysts may be undergoing morphological and/or chemical changes. Conditioning may also be related to wetting of the metal catalyst layer with the polymer electrolyte. The conditioning process can take from 1 to 3 days. For initial screening of a catalyst, at least three days of data acquisition are required after the conditioning process. Thus with a single cell, the testing of one catalyst requires 4 to six days of conditioning and data acquisition. In order to include a statement of uncertainty with the final result, the catalysts should be repetitively tested with 4 to 6 sample of the catalyst. Thus the testing one catalyst with statistical reliability requires at least 25 days of continuous test stand operation. The comparison of 5 catalysts reliably would take 125 days of testing. Preparation of the electrodes would require about 4 additional days. 129 days of test stand operation including weekends off would require almost 200 days. These timelines are difficult ranges for small businesses testing catalysts with short delivery times. Finally, the above type to testing on single cell systems is not reliable because each single cell test requires the assumption that the common electrode is performing the same for each and every test. The likelihood of 125 days of test stand operation having uniform cathode performance is very low. Thus it is likely that the time required for reliable testing should be about doubled. Thus, it can take over a year to test and compare 5 catalysts and this timeframe would not permit lifetime studies.

It has been over 30 years since PtRu was found to be the best but inadequate catalysts for DMFCs. If new catalysts are to be discovered, new high throughput screening methods will be required and that is the motivation for this invention.

SUMMARY OF THE INVENTION

An object of the present invention is a single cell fuel cell assembly having standard graphite flow field block for one electrode and an array flow field block for contact to the side of the membrane electrode assembly incorporating the array of catalyst to be simultaneously tested.

An embodiment of this invention is a high throughput screening device for combinatorial chemistry, comprising a membrane electrode assembly, one or more common electrodes and an array of sensor electrodes wherein a total cross-sectional area of the one or more common electrodes is greater than a sum of the cross-sectional areas of the sensor electrodes and the device does not require a movement of any electrode during data acquisition. Another embodiment is a high throughput screening device for combinatorial chemistry, comprising a membrane electrode assembly, one or more common electrodes and an array of sensor electrodes wherein a total cross-sectional area of the one or more common electrodes is greater than a sum of the cross-sectional areas of the sensor electrodes and the array of sensor electrodes are operated simultaneously.

The array of sensor electrodes are capable of being operated simultaneously in a fuel cell. The device could further comprise a catalyst. The catalyst could be a fuel cell catalyst. The catalyst could be applied to a carbon diffusion layer or to a membrane. The membrane electrode assembly could comprise an electrolyte layer and two catalyst layers. The electrolyte layer could be a polymer membrane. The device could further comprise a gas diffusion layer and a flow field block. The device could further comprise a current follower and a potential follower. The sensor electrode could comprise graphite. The membrane electrode assembly could comprise an electronically insulating proton conductor.

Additional advantages of this invention would become readily apparent to those skilled in this art from the following detailed description, wherein only the preferred embodiments of this invention are shown and described, simply by way of illustration of the best mode contemplated for carrying out this invention. As would be realized, this invention is capable of other and different embodiments, and its details are capable of modifications in various obvious respects, all without departing from this invention. Accordingly, the drawings and description are to be regarded as illustrative in nature and not as restrictive.

DETAILED DESCRIPTION

Figure 1:
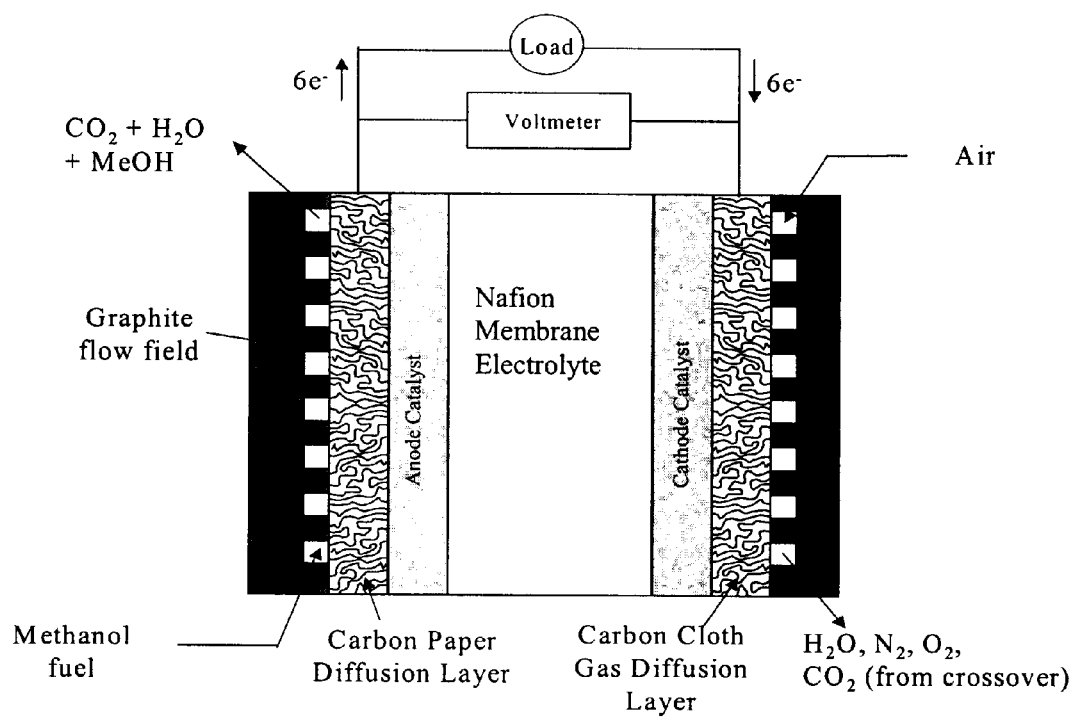
FIG. 1 shows a schematic of a fuel cell not drawn to scale.

As used herein, the term "proton conductor" refers to any body capable of conducting protons. The body could be a single material or a composite material. A composite material is a materials system composed of a mixture or combination of two or more macro constituents differing in form and/or material composition and that are essentially insoluble in each other.

For purposes of this invention, a MEA comprises at least an electrode layer, e.g., an anode or a cathode, where a chemical entity is oxidized or reduced respectively, and a common electrode, e.g., a cathode or an anode, where an oxidant is reduced or a fuel is oxidized respectively. The MEA also has an EIPC, which conducts protons, but not electrons. The EIPC of this invention could be a separate component of the MEA or incorporated into a graded layer that is electronically insulating yet proton conductive on one face and a mixed electronic-protonic conductor on the opposite face. The mixed conductor region would serve as the catalytic region and the electronically insulating region would serve as the electrolyte or EIPC. A catalytic layer would be supported on the EIPC side of the graded layer. This would constitute a 2 layer MEA. This two-layer MEA would generally be operated at a high temperature such that one side of the proton conducting composite membrane of the MEA would not require a catalytic layer because the reaction at the uncatalyzed side is facile because of the high temperature. A generic representation for the MEA is: Anode/EIPC/Cathode. A two layer MEA would be one where one of the electrode regions has a gradually changing interface separating the EIPC region from the electrode region. This invention encompasses several embodiments of MEA.

Another embodiment of a two-layer MEA would be an electrode and a common electrode sandwiched together, wherein the interface between the electrode and common electrode forms an EIPC. An embodiment of a three-layer system would have an EIPC with catalytic layers of electrode and common electrode on both sides of the EIPC. The polymer electrolyte fuel cell MEA using Nafion with catalyst layers on both sides of Nafion is an example of a three layer MEA.

In another embodiment, a 5-layer MEA, an anode catalytic layer is supported on an EIPC, which in turn, is supported on a metal hydride foil. The face of the foil opposite the anode can have an EIPC layer deposited on the surface upon which is interfaced the cathode catalytic layer. Another embodiment, a 4-layer MEA, would have the EIPC on only one side of the metal hydride foil.

In general, an MEA is a component of a fuel cell, which includes the electrolyte system sandwiched between an anode and a cathode catalytic layer. The electrolyte system can include a matrix that supports a liquid phase electrolyte, a polymer phase, an inorganic phase that conducts oxide, carbonate or protons. The electrolyte can be a multicomponent system. The anode catalyst could be a high surface area platinum/ruthenium mixed metal catalyst (PtRu) and the cathode could be high surface area Pt black catalyst. The shorthand notation for a MEA having a PtRu anode, an EIPC and a Pt cathode is: PtRu/EIPC/Pt.

In a fuel cell, the polymer electrolyte membrane (e.g. Nafion™ in a polymer electrolyte fuel cell) is catalyzed on both faces. One face is the anode side where fuel is oxidized and the opposite face is the cathode side where oxygen is reduced. This three-layer system is commonly referred to as a membrane electrode assembly (MEA). The membrane electrode assembly is inserted into a fuel cell assembly. FIG. 1 is a schematic of a fuel cell assembly. In one embodiment, the membrane assembly is a Nafion membrane electrolyte including the two catalytic layers that sandwich the membrane. There are two primary methods by which the catalysts can be incorporated into the fuel cell assembly. The catalyst can be (1) applied to a carbon diffusion layer or (2) applied to a membrane.

When the catalyst layer is applied to the carbon, the cell is assembled as follows: One of the graphite flow fields is laid upon a flat surface. The catalyzed carbon paper is laid upon the graphite flow fields with the catalyst layer facing upward. The Nafion layer is laid upon the catalytic surface. The next catalyzed carbon paper is laid upon the Nafion with the catalyst side placed in contact with the Nafion. The second graphite flow field is laid upon the unmodified surface of the carbon paper and the cell is then bolted together.

The catalyst can also be decal transferred to the Nafion layer by the method of M. S. Wilson et al., *J. Appl. Electrochem.*, Vol. 22, 1 (1992). The cell is assembled in the same manner as above using pristine carbon diffusion layers. The final two assemblies of an embodiment of this invention correspond to the schematic depicted in FIG. 1.

A membrane electrode assembly is prepared with one side to face the large common electrode and the other side to face the twenty-five separate working electrodes (i.e. the twenty five sensor electrodes). Since the common electrode is about five times larger that the sum of the cross-sectional areas of the working electrodes, the common electrode can be used as a reference electrode as well. This is an advantage of using a total cross-sectional area of the one or more common electrodes greater than a sum of the cross-sectional areas of the sensor electrodes.

Hydrogen will pass through the common electrode. Fuel (e.g. methanol, reformate, etc) will flow through the working electrode array flow fields. A series of potential points programmed by computer will be applied between the common electrode and all of the array working electrodes simultaneously. At each potential, the steady current will be sensed by the National Instruments data acquisition card and recorded by the computer. The current-voltage data is commonly referred to as the performance curves. In this invention, "simultaneously" refers to data acquisition from the array of working electrodes at the same time or with a time difference such that the data acquired is substantially the same as that obtained by acquiring data from the array of working electrodes at the same time.

FIG. 1 shows a schematic of a fuel cell not drawn to scale. The drawing shows the outer flow field blocks constructed of graphite. The graphite blocks contact the gas diffusion layers (GDLs) that comprise either of carbon paper or carbon cloth. The GDLs contact the catalyst layers. The catalyst layers sandwich the polymer electrolyte (e.g. Nafion 117). The MEA within this drawing is the tri-layer comprising of the Polymer membrane and the two catalyst layers. When the catalyst layers are deposited on the GDLs, the GDLs can be considered part of the MEA. The fuel cell utilizes an array MEA where one side of the MEA is conventional and the opposite side is an array of catalytic spots.

Figure 2:
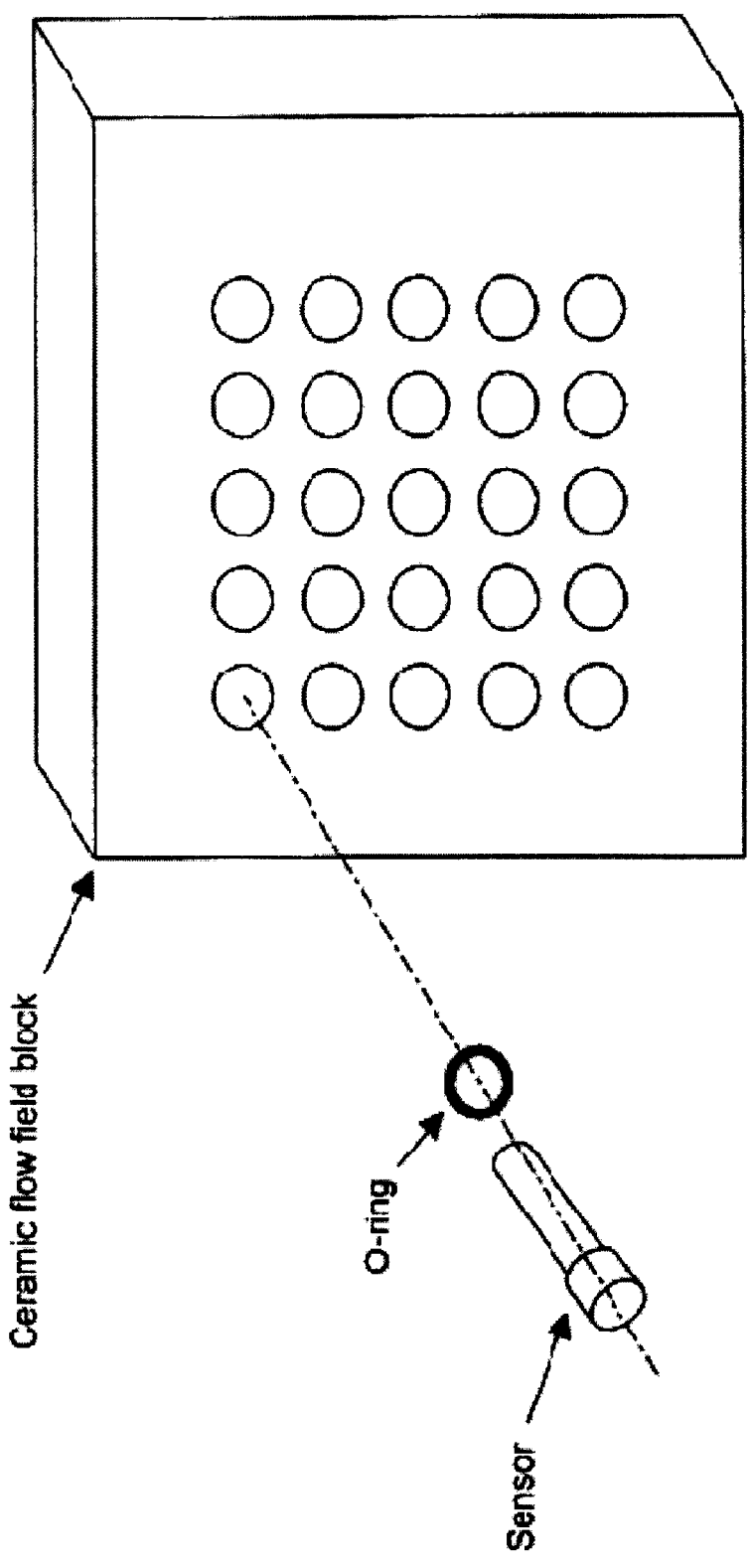
FIG. 2 shows a schematic of a flow field block having holes in which sensor electrodes are attached using an O-ring for sealing.

FIG. 2 shows a schematic of a flow field block having holes in which sensor electrodes are attached using an O-ring for sealing. In particular, FIG. 2 shows a flow field block having 25 holes. However, the device of this invention is not limited to a flow field block having 25 holes but could contain any number of holes greater than 1.

Figure 3:
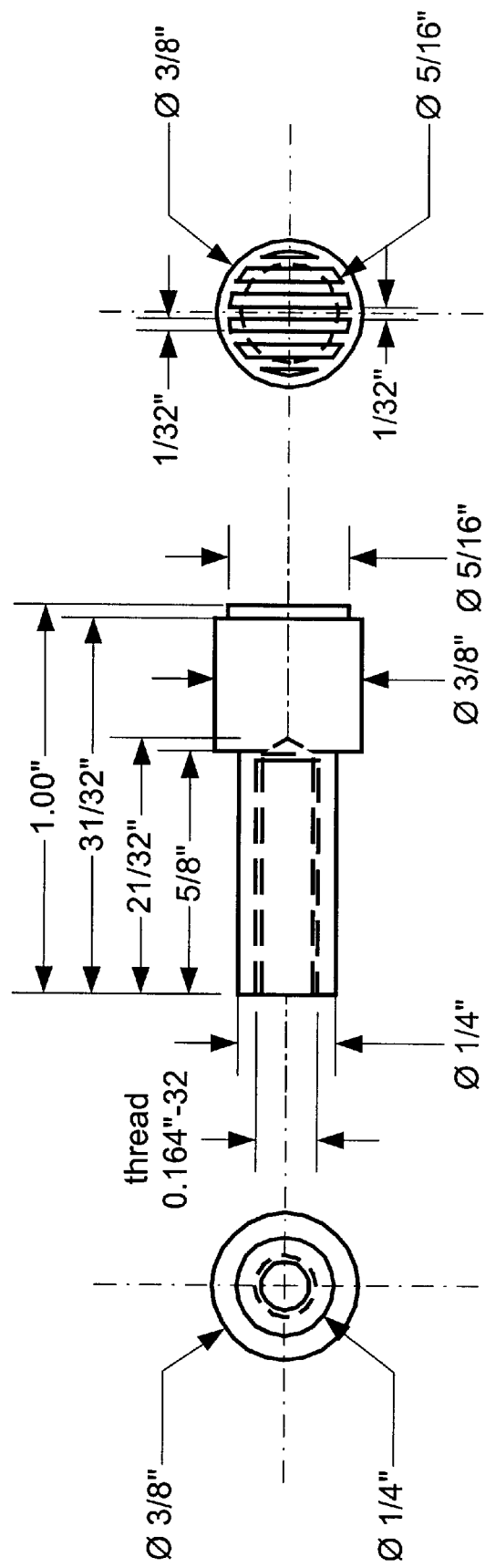
FIG. 3 shows a schematic of a sensor electrode.

FIG. 3 is a machinist drawing of a single sensor electrode, preferably a graphite sensor electrode, of an embodiment of this invention. The dimensions shown in FIG. 3 and other figures in this application are for illustrative purposes only and the device and method of this invention is limited to using these dimensions shown in the figures.

Figure 4:
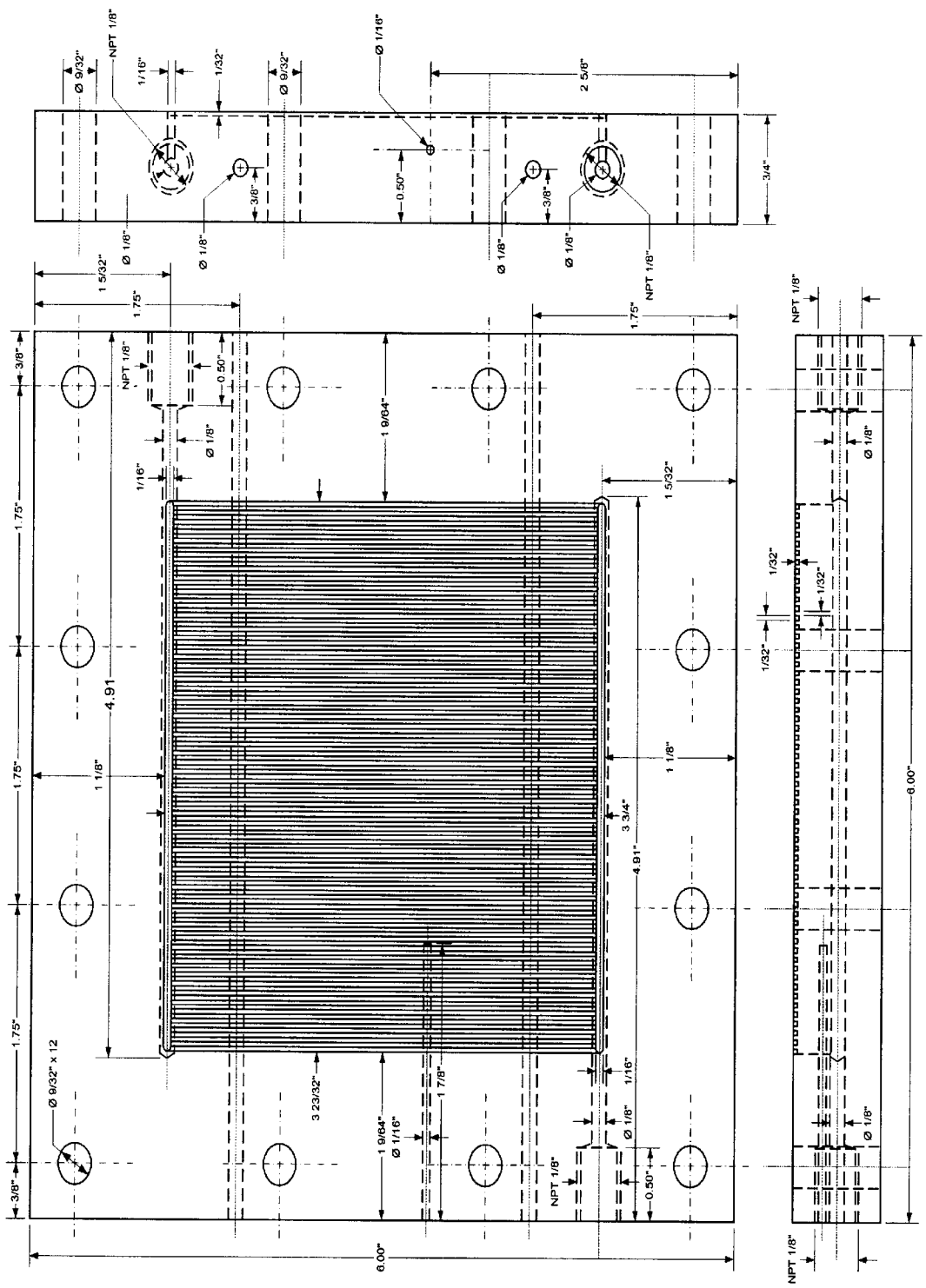
FIG. 4 shows a single common electrode.

FIG. 4 shows a single common electrode. One can see the inlet and the outlet of the system where the NPT pipe threads are. The square region of flow field is located in the center of the block. The reactant feed enters the flow field through an NPT fitting, is forced across the flow fields and then out the NPT outlet. As the gas flow across the flow fields some of the gas diffuses across the GDL and reacts at the catalytic surface. The central area is grooved to guide the reactant gas or liquid over the unmodified face of the carbon gas diffusion layer (GDL). The reactant diffuses through the GDL to the catalytic surface where either oxidation or reduction occurs at anode or cathode surfaces respectively. There are twelve holes in the block for bolts.

Figure 5:
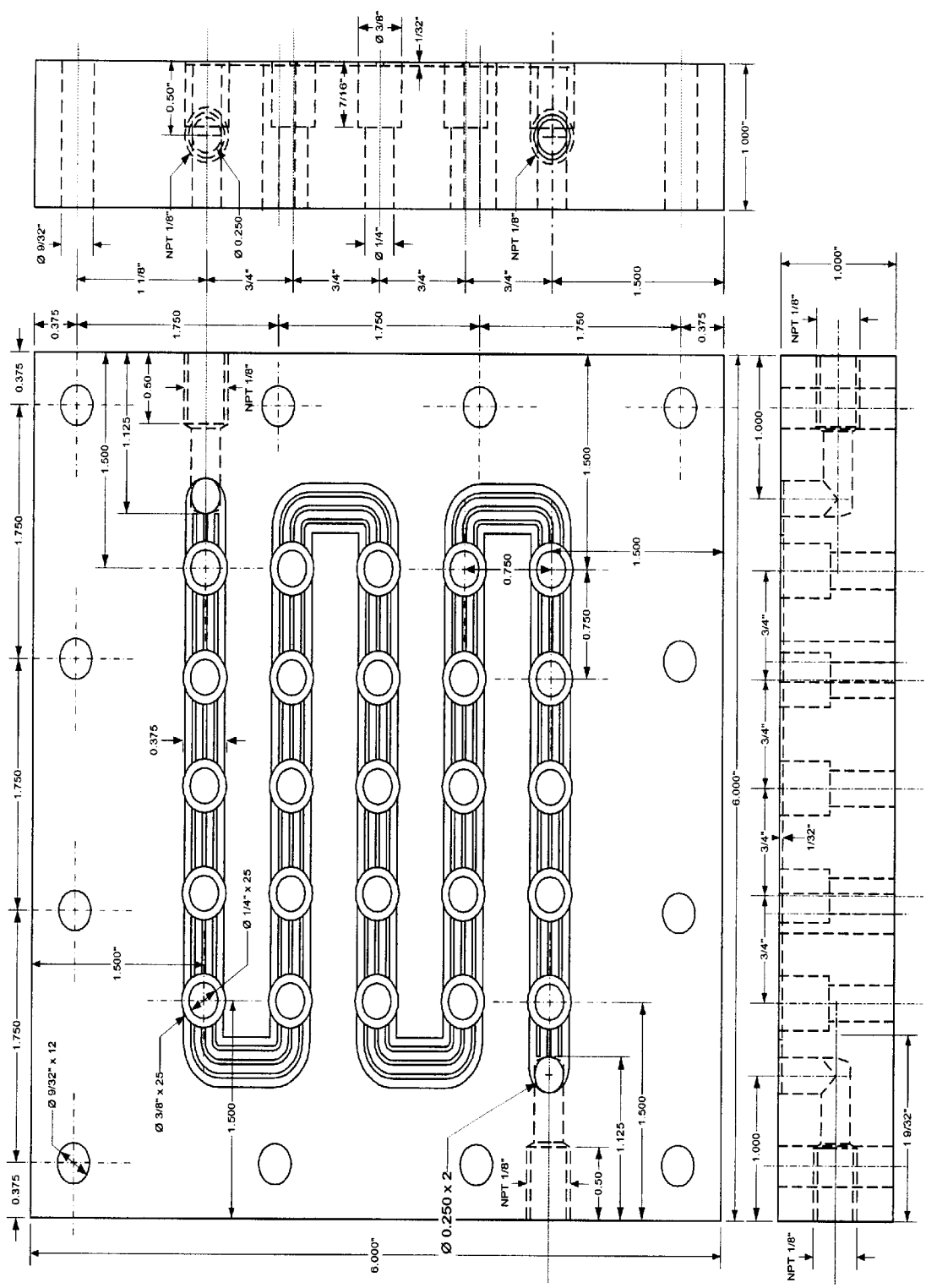
FIG. 5 shows a flow field block for an array of sensor electrodes.

FIG. 5 shows the flow field block for the array side of the fuel cell. The array block comprises a non-conductive material such as Teflon or ceramics. The key criteria for selection of the material is that the material be not electronically conducting and that the material has an expansion coefficient that is small relative to Teflon and not too different from graphite. We use ceramic as our array block because the thermal expansion coefficient of Teflon is too large and as the cell is heated to the operating temperature (between 40° C. and 100° C.) the assembly tends to distort from the configuration it had when bolted together at room temperature. The thermal expansion coefficient is smaller for ceramics, thus ceramics permit a wider temperature range of operation for the array system.

In one embodiment of this invention, there are flow field grooves in FIG. 5 that connect the 25 spots in series. The block has 25 holes in it where sensor electrodes are glued in. The sensor electrodes are graphite sensor electrodes with miniature flow fields incorporated on the surface of the sensor electrodes. Just as in FIG. 4, there is an NPT inlet and outlet. However, now the flow field is simply a narrow field that directs the flow to 25 holes in the block. The 25 holes are connected in series. The holes are meant to accommodate the press fitting or gluing of the sensor electrodes.

In one embodiment, twenty-five of the sensor electrodes of FIG. 3 are inserted into the twenty-five holes of the array block of FIG. 5. The sensor electrode is designed to fit into the holes of the block shown in FIG. 2. The surface of the sensor electrode, which would be aligned with the linear flow field of the block depicted in FIG. 5, has flow field grooves on the surface. In one embodiment, the grooves are 1/32" wide. It is the grooves of the sensor electrode that will contact the GDLs of the array electrode region. The narrow side of the sensor electrode is threaded. The thread is designed to accommodate a screw lead that contacts a wire for delivery of current to the current follower. Each sensor electrode has a screw lead that electronically connects the sensor electrode to a current follower circuit.

Figure 6:
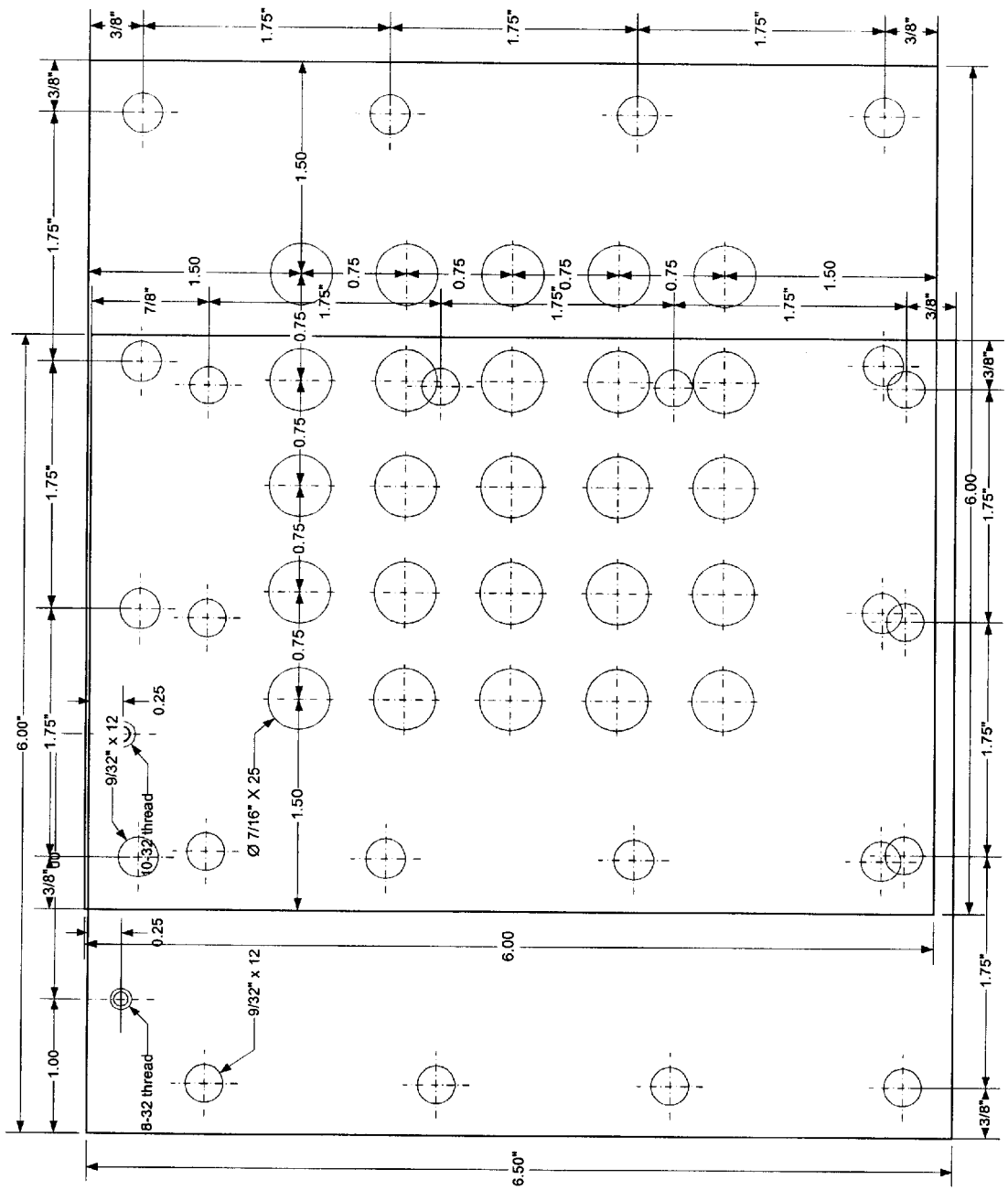
FIG. 6 shows sensor electrodes incorporated into the flow field block for an array of sensor electrodes.

FIG. 6 shows, as an embodiment of this invention, how the sensor electrodes are incorporated into the ceramic block of FIG. 5. Each sensor electrode is connected to an electronic lead on the backside of the flow field block (i.e. the side opposite from the flow fields), which is shown in FIG. 6. The electronic lead from the sensor electrode is attached to a current follower, which converts the current into a potential that can be sensed by a commercial data acquisition card. The data acquisition card used in this work is a National Instruments card. A schematic of the current follower circuit of an embodiment of this invention is shown in FIG. 7.

Figure 7:
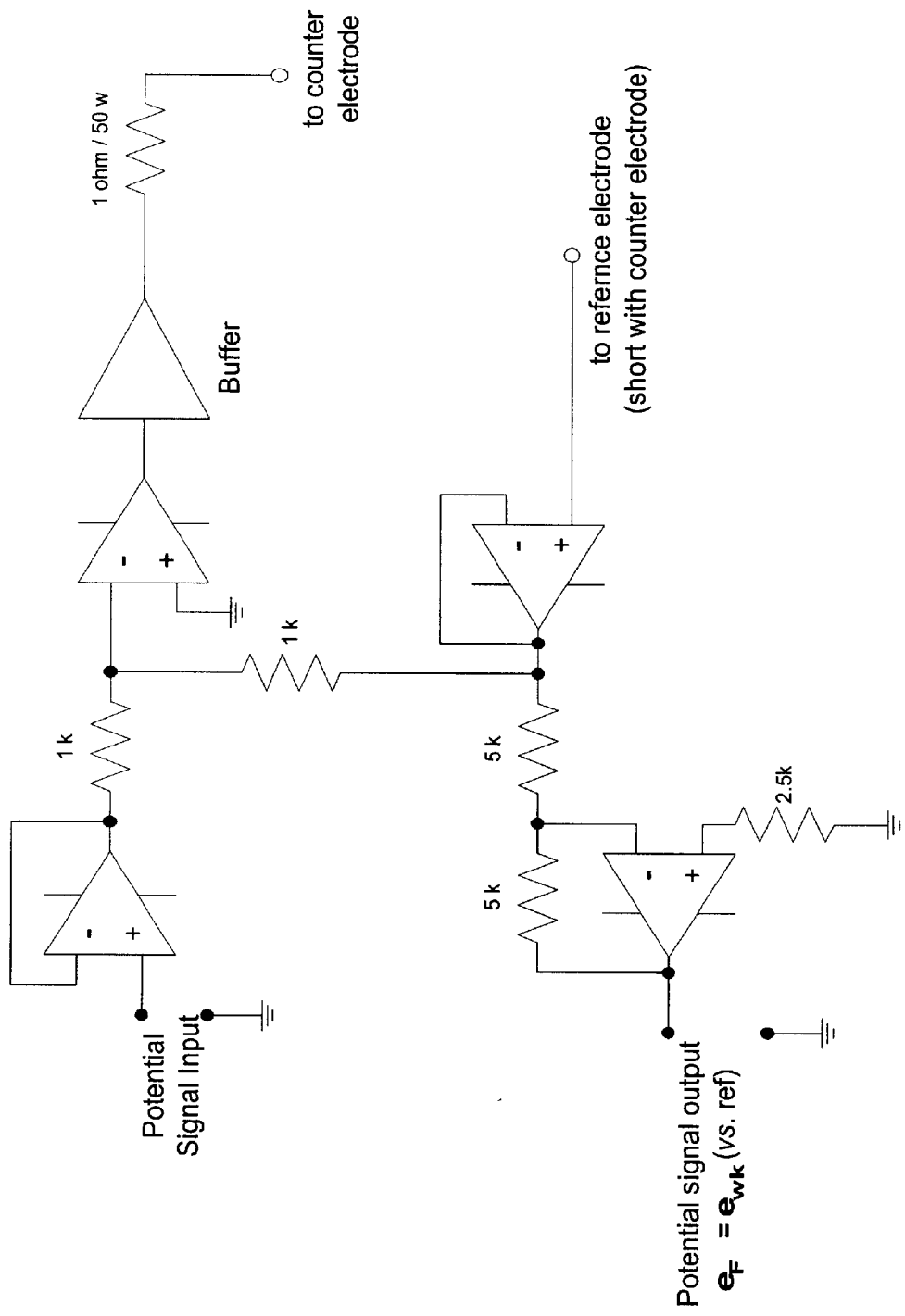
FIG. 7 is a circuit diagram of the current follower to which the wire from the back of the sensor electrode is input.

FIG. 7 is a circuit diagram of the current follower to which the wire from the back of the sensor electrode is input. This circuit is a standard operational amplifier circuit for current followers.

A potential follower circuit maintains the voltage of the common electrode in comparison to the array electrodes. The circuit used in an embodiment of this invention is shown in FIG. 8.

Figure 8:
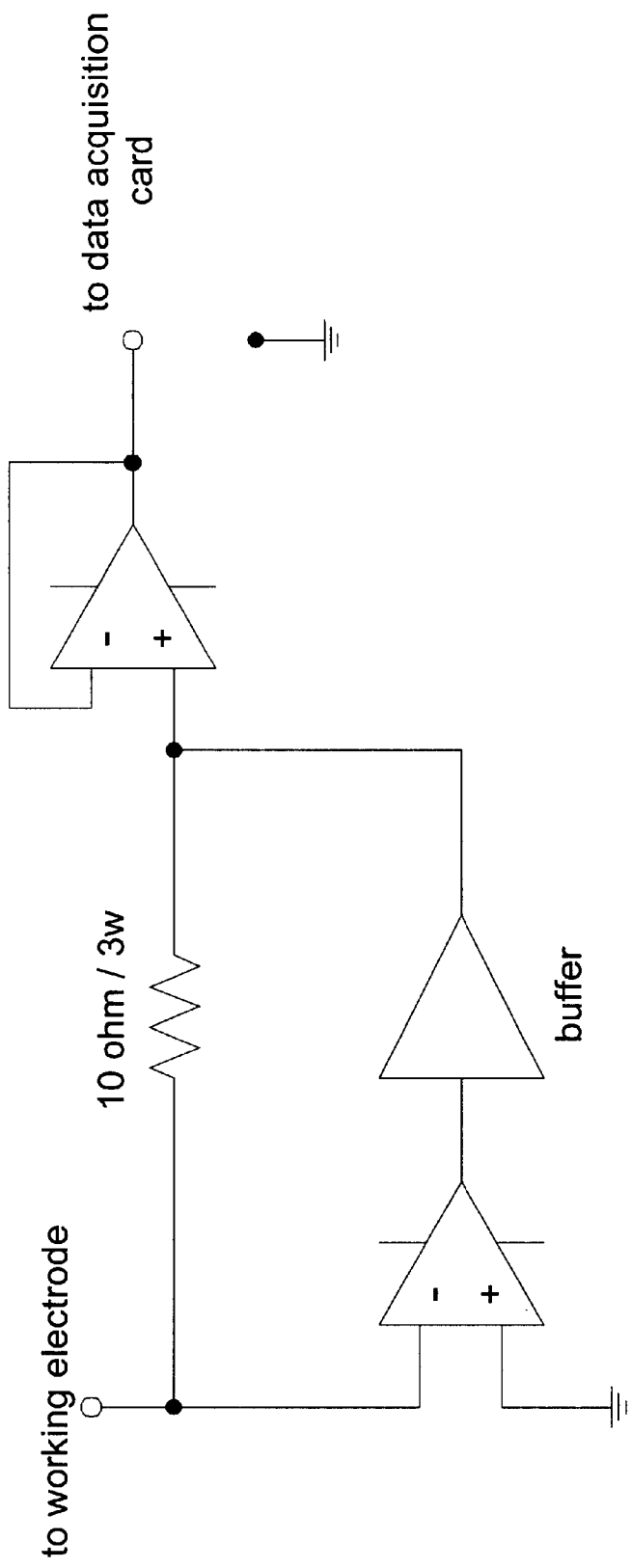
FIG. 8 shows the schematic for the voltage follower used to control the potential of the flow field block for an array of sensor electrodes.

FIG. 8 shows the schematic for the voltage follower that is used to control the potential of the block depicted in FIG. 3 versus the potential of each and every sensor electrode unit (25 in all in this description). The output of the potential follower module is fed to the same National Instruments data acquisition card used by the array of current followers.

Figure 9:
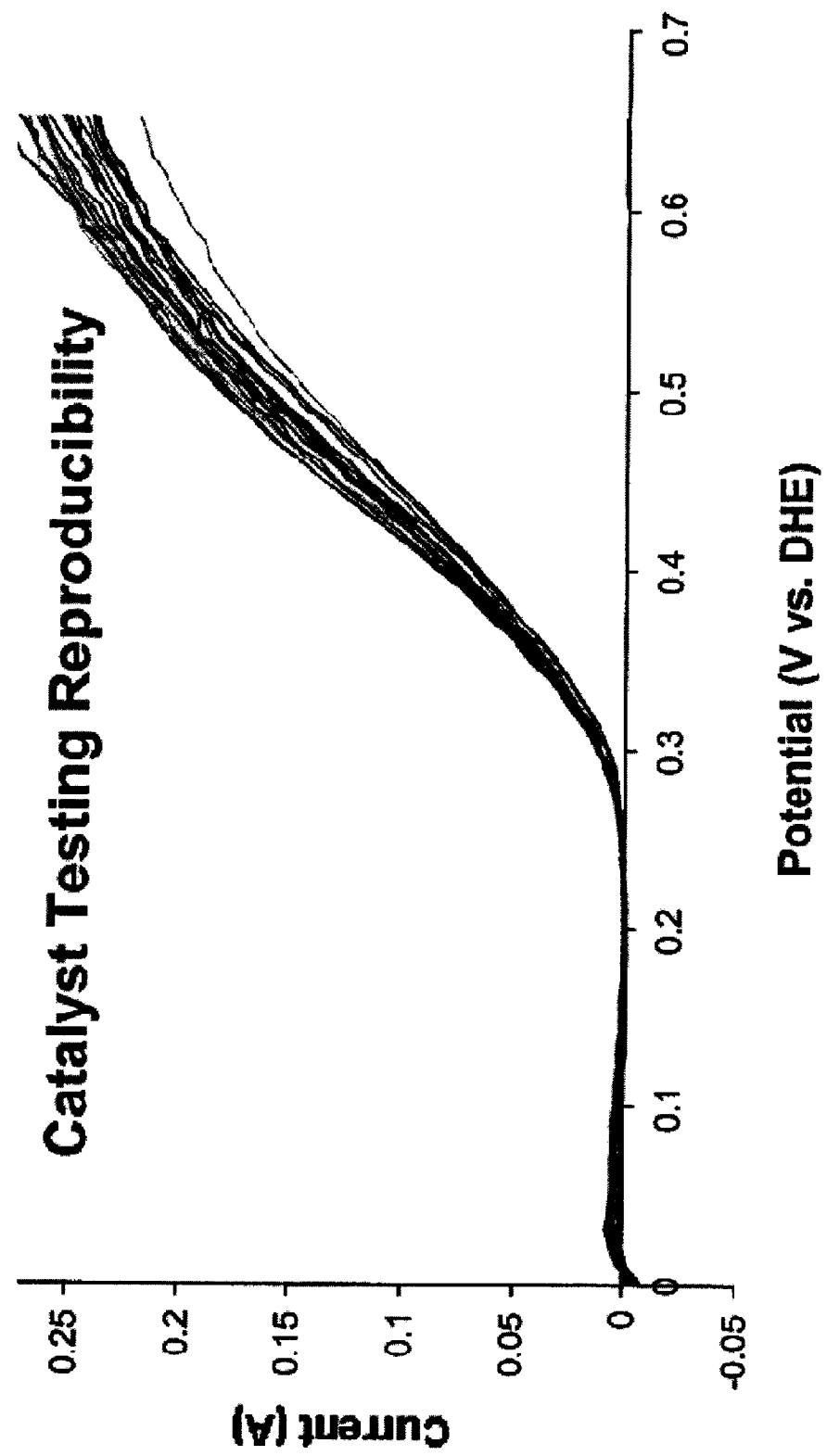
FIG. 9 shows data obtained from the device of this invention. The y axis shows the current being delivered to the current follower for each of the twenty five sensor electrodes and the x-axis shows the potential of the anode sensor electrodes.

FIG. 9 shows data obtained from the device of this invention for a device having 25 sensor electrodes. The y axis shows the current being delivered to the current follower for each of the twenty five sensor electrodes. The x-axis shows the potential of the anode sensor electrodes. The potential on the x axis represents the difference between the potential of the array electrodes from the larger common electrode. At an instance, all of the array electrodes are at the same potential although electronically insulated from each other. The figure of merit is the current. At any particular potential, the larger the current, the better the candidate. The data of FIG. 9 shows the spread that this technique has since all 25 electrodes were composed of the same material.

In particular, FIG. 9 shows 25 catalyst performance curves obtained by testing 25 catalyst samples simultaneously. The curves of FIG. 9 were obtained after conditioning the array for two days. Then all the data acquisition for all 25 catalysts spots were obtained in one day. This is much faster than if serial testing ad been carried out individually for each sample.

The variable of merit in FIG. 9 is the current. At any particular potential, the larger the current, the better the candidate. The data of FIG. 9 shows the spread that this technique has since all 25 electrodes were composed of the same material. For direct methanol fuel cells, a relevant current is the current obtained when the voltage is between the 0.3 and 0.4 volts.

Besides using the device of this invention for combinatorial chemistry to develop new catalysts, applicants found another important application for the device. A key area of fuel cell development, both reformate and direct methanol fuel cells, is the development of new membranes. With each new membrane comes the requirement for a new membrane electrode assembly (MEA) fabrication method. This will typically involve making a dispersion of the catalyst in a liquid consisting of ordinary organic solvents (e.g. alcohol, glycerol, etc) and some of the solubilized un-cross linked polymer used as the electrolyte. This dispersion is known as the catalyst "ink." Optimizing the preparative method for ink is a complex, laborious process. The parameters that must be optimized include:

1) what ingredients should be included in the ink
2) how much of each ingredient should be in the ink
3) in what order should the ingredients be added
4) what type of stirring should be done
5) how long should the ink be stirred This type of multi-parameter optimization is best addressed by preparative combinatorial methods, as this will dramatically reduce the time required for optimization.

Given a new polymer membrane, 25 different ink preparative methods can be tried by the device of FIG. 2. An MEA with a common cathode and 25 anode catalytic spots or 25 cathode catalytic spots with a common anode can be inserted into the device. Polarization curves can then be obtained for 25 electrodes in two days. To do the same testing with 25 standard test stands would require about half a million dollars of test stands and 5 employees. Applicants' device can do it about two days using the device of FIG. 2, which is estimated to cost about $40,000, with one employee.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

This application discloses several numerical range limitations. Persons skilled in the art would recognize that the numerical ranges disclosed inherently support any range within the disclosed numerical ranges even though a precise range limitation is not stated verbatim in the specification because this invention can be practiced throughout the disclosed numerical ranges. A holding to the contrary would "let form triumph over substance" and allow the written description requirement to eviscerate claims that might be narrowed during prosecution simply because the applicants broadly disclose in this application but then might narrow their claims during prosecution. Finally, the entire disclosure of the patents and publications referred in this application are hereby incorporated herein by reference.

What is claimed is:

1. A high throughput screening device for combinatorial chemistry, comprising:
   a membrane electrode assembly,
   one or more common electrodes and
   an array of sensor electrodes
   wherein a total cross-sectional area of the one or more common electrodes is greater than a sum of the cross-sectional areas of the sensor electrodes and the device does not require a movement of any electrode during data acquisition.

2. The device of claim 1, wherein the array of sensor electrodes are capable of being operated simultaneously in a fuel cell.

3. The device of claim 1, wherein the device further comprises a catalyst.

4. The device of claim 3, wherein the catalyst is a bulk electrocatalyst.

5. The device of claim 4, wherein the catalyst is applied to a membrane.

6. The device of claim 1, wherein the membrane electrode assembly comprises an electrolyte layer and two catalyst layers.

7. The device of claim 6, wherein the electrolyte layer is a membrane.

8. The device of claim 1, further comprising a flow field block.

9. The device of claim 8, further comprising a current follower and a potential follower.

10. The device of claim 1, wherein the sensor electrode comprises graphite.

11. A high throughput screening device for combinatorial chemistry, comprising:
   a membrane electrode assembly,
   one or more common electrodes and
   an array of sensor electrodes
   wherein a total cross-sectional area of the one or more common electrodes is greater than a sum of the cross-sectional areas of the sensor electrodes and the array of sensor electrodes are operated simultaneously.

12. The device of claim 11, wherein the device further comprises a catalyst.

13. The device of claim 12, wherein the catalyst is bulk electrocatalyst.

14. The device of claim 13, wherein the catalyst is applied to a membrane.

15. The device of claim 11, wherein the membrane electrode assembly comprises an electrolyte layer and two catalyst layers.

16. The device of claim 15, wherein the electrolyte layer is a membrane.

17. The device of claim 11, further comprising a flow field block.

18. The device of claim 17, further comprising a current follower and a potential follower.

19. The device of claim 11, wherein the sensor electrode comprises graphite.

20. The device of claim 11, wherein the membrane electrode assembly comprises an electrolyte.

* * * * *